(12) United States Patent
Pedro

(10) Patent No.: US 10,888,274 B2
(45) Date of Patent: *Jan. 12, 2021

(54) METHOD FOR DIAGNOSIS OF AND THERAPY FOR A SUBJECT HAVING A CENTRAL NERVOUS SYSTEM DISORDER

(71) Applicant: Victor M. Pedro, Cranston, RI (US)

(72) Inventor: Victor M. Pedro, Cranston, RI (US)

(*) Notice: Subject to any disclaimer, the term of this patent is extended or adjusted under 35 U.S.C. 154(b) by 0 days.

This patent is subject to a terminal disclaimer.

(21) Appl. No.: 14/033,004

(22) Filed: Sep. 20, 2013

(65) Prior Publication Data

US 2014/0135590 A1  May 15, 2014

Related U.S. Application Data

(60) Provisional application No. 61/726,511, filed on Nov. 14, 2012.

(51) Int. Cl.
| | |
|---|---|
| *A61B 5/00* | (2006.01) |
| *A61B 5/0205* | (2006.01) |
| *A61B 3/11* | (2006.01) |
| *A61B 5/11* | (2006.01) |
| *A61B 5/1455* | (2006.01) |
| *A61N 1/18* | (2006.01) |

(52) U.S. Cl.
CPC ............ *A61B 5/4884* (2013.01); *A61B 3/112* (2013.01); *A61B 5/0205* (2013.01); *A61B 5/1118* (2013.01); *A61B 5/14551* (2013.01); *A61B 5/4058* (2013.01); *A61B 5/4076* (2013.01); *A61B 5/4266* (2013.01); *A61N 1/18* (2013.01)

(58) Field of Classification Search
CPC ......... A61B 5/0205; A61B 5/103; A61B 5/11; A61B 5/1116; A61B 5/4035; A61B 5/4076; A61B 5/4082; A61B 5/4266; A61B 5/4884
USPC .......................... 600/300, 301; 128/897, 898
See application file for complete search history.

(56) References Cited

U.S. PATENT DOCUMENTS

| | | | | |
|---|---|---|---|---|
| 5,267,942 A | * | 12/1993 | Saperston | ............. A61M 21/02 128/905 |
| 5,299,119 A | * | 3/1994 | Kraf et al. | ..................... 600/509 |

(Continued)

OTHER PUBLICATIONS

"Rebuilding Sidney Crosby's brain" http://www.macleans.ca/society/rebuilding-crosbys-brain/ (dated Nov. 3, .2011).*

(Continued)

*Primary Examiner* — Nathan J Jenness
(74) *Attorney, Agent, or Firm* — Sunstein LLP

(57) ABSTRACT

A method is provided of systematically evaluating and treating dynamic autonomic dysregulation in a subject. The method includes having the subject sequentially assume a plurality of distinct postures that may include, for example, walking, standing, sitting or supine. In each posture of the subject, the subject is subjected to sensory stimulation while measuring at least one autonomic physiological response of the subject. The autonomic physiological response may include, for example, oxygen saturation, heart rate, pupillary response, blood pressure, sweat production, pseudomotor activity or respiration. The physiological responses in each of the distinct postures are evaluated to identify a posture wherein the subject exhibits a least amount of dysfunction.

7 Claims, 6 Drawing Sheets

(56) References Cited

U.S. PATENT DOCUMENTS

| | | | | |
|---|---|---|---|---|
| 6,007,459 | A * | 12/1999 | Burgess | 482/4 |
| 6,685,729 | B2 * | 2/2004 | Gonzalez | 607/1 |
| 2004/0158297 | A1 * | 8/2004 | Gonzalez | A61B 5/16 607/45 |
| 2005/0056290 | A1 * | 3/2005 | Feinberg | 128/898 |
| 2007/0161912 | A1 * | 7/2007 | Zhang et al. | 600/483 |
| 2008/0171923 | A1 * | 7/2008 | Bolea et al. | 600/301 |
| 2008/0256686 | A1 * | 10/2008 | Ferrara | A41D 13/0155 2/413 |

OTHER PUBLICATIONS

"Chiropractic Neurology: Breakthrough Treatment of Placebo?" http://abcnews.go.com/Health/chiropractic-neurology-breakthrough-placebo/story?id=17027630&singlePage=true (dated Aug. 17, 2012).*

Gao et al. "Brain-modulated Effects of Auricular Acupressure on the Regulation of Autonomic Function in Healthy Volunteers" Evidenced-Based Complementary and Alternative Medicine vol. 2012.*

Yokota Y, Aoki M, Mizuta K, Ito Y, Isu N.. Motion sickness susceptibility associated with visually induced postural instability and cardiac autonomic responses in healthy subjects. Acta Otolaryngol (2005)125(3):280-5.10.1080/00016480510003192.*

Judith F. Fleuren, Mark J. Nederhand, Hermie J. Hermens, Influence of Posture and Muscle Length on Stretch Reflex Activity in Poststroke Patients With Spasticity, Archives of Physical Medicine and Rehabilitation, vol. 87, Issue 7, Jul. 2006, pp. 981-988, ISSN 0003-9993, http://dx.doi.org/10.1016/j.apmr.2006.03.018.*

Llinás, et al., *The neuronal basis for consciousness*, Phil. Tran. R. Soc. Lond. B (The Royal Society), vol. 353, No. 1377, pp. 1841-1849, Nov. 1998.

Llinás, et al., *Thalamocortical dysrhythmia: a neurological and neuropsychiatric syndrome characterized by magnetoencephalography*, PNAS, vol. 96, No. 26, pp. 15222-15227, Dec. 1999.

Llinás, *Temporal binding via coincidence detection of specific and nonspecific thalamocortical inputs: A voltage-dependent dye-imaging study in mouse brain slices*, PNAS (The National Academy of Sciences) vol. 99, No. 1, pp. 449-454, 2002.

Damasio et al., *Minding the Body*, Daedalus, vol. 135, No. 3, pp. 15-22, 2006.

Leigh et al., *Neuroscience of Eye Movements*, published by ACNR, vol. 5, No. 6, pp. 12-15, Jan./Feb. 2006.

Jones, *Thalamocortical dysrhythmia and chronic pain*, Pain (Elsevier) 150: 4-5, 2010.

Damasio, Looking for Spinoza: Joy, Sorrow, and the Feeling Brain, A Harvest Book, Harcourt, Inc., 2003.

Damasio, Descartes' Error: Emotion, Reason, and the Human Brain, Penguin, 2005.

Leigh et al., The Neurology of Eye Movements, Contemporary Neurology Series, 4th Edition, Oxford University Press, 2006.

Llinás et al., The Mind-Brain Continuum: Sensory Processes, A Bradford Book, The MIT Press, 1996.

Llinás, I of the Vortex: From Neurons to Self, A Bradford Book, The MIT Press, 2001.

United States Patent and Trademark Office, Office Action dated Oct. 10, 2014 pertaining to U.S. Appl. No. 14/284,864, 16 pages.

United States Patent and Trademark Office, Applicant-Initiated Interview Summary dated Dec. 29, 2014 pertaining to U.S. Appl. No. 14/284,864, 3 pages.

Sunstein Kann Murphy & Timbers LLP, Response to Office Action dated Oct. 10, 2014 pertaining to U.S. Appl. No. 14/284,864, 26 pages.

United States Patent and Trademark Office, Office Action dated Mar. 23, 2015 pertaining to U.S. Appl. No. 14/284,864, 11 pages.

Sunstein Kann Murphy & Timbers LLP, Request for Continued Examination and Response pertaining to U.S. Appl. No. 14/284,864 dated Sep. 21, 2015, 21 pages.

United States Patent and Trademark Office, Office Action dated Nov. 30, 2015 pertaining to U.S. Appl. No. 14/284,864, 14 pages.

* cited by examiner

FIG. 5

P02 Patient Log

Patient Name: _____ Date: _____

| P/O2 | SEATED: HR | | | STANDING: HR | | | SUPINE: HR | | | VISUAL: HR | | | AUDITORY: HR | | | TEMP: HR | | |
|---|---|---|---|---|---|---|---|---|---|---|---|---|---|---|---|---|---|---|
| | | L | R | | L | R | | L | R | | L | R | | L | R | | L | R |
| Neutral | | | | | | | | | | | | | | | | | | |
| Left Rotation | | | | | | | | | | | | | | | | | | |
| Right Rotation | | | | | | | | | | | | | | | | | | |
| Flexion | | | | | | | | | | | | | | | | | | |
| Extension | | | | | | | | | | | | | | | | | | |
| Downward Gaze | | | | | | | | | | | | | | | | | | |
| Upward Gaze | | | | | | | | | | | | | | | | | | |
| RtWard Gaze | | | | | | | | | | | | | | | | | | |
| LtWard Gaze | | | | | | | | | | | | | | | | | | |
| UpLeft Gaze | | | | | | | | | | | | | | | | | | |
| DownLeft Gaze | | | | | | | | | | | | | | | | | | |
| UpRight Gaze | | | | | | | | | | | | | | | | | | |
| DownRight Gaze | | | | | | | | | | | | | | | | | | |

Pulse Oximetry / Blood Pressure / Respiration Rate / Temp

| | B/P | Temp. | Resp. |
|---|---|---|---|
| Left | | | |
| Right | | | |

CIT PATIENT LOG          Patient Name: _____          Date: _____

| HEAD POSITION | BASE HR | BASELINE STAB/ FATIGUE | TENS HR | TENS L R | TEMP HR | TEMP L R | VISUAL HR | VISUAL L R | AUD HR | AUDITORY L R | TMJ HR | TMJ L R | OTHER HR | OTHER EFFERENTCOPY HAPTIC VIBRATORY |
|---|---|---|---|---|---|---|---|---|---|---|---|---|---|---|
| Neutral | | | | | | | | | | | | | | |
| Left Rotation | | | | | | | | | | | | | | |
| Right Rotation | | | | | | | | | | | | | | |
| Flexion | | | | | | | | | | | | | | |
| Extension | | | | | | | | | | | | | | |
| Downward Gaze | | | | | | | | | | | | | | |
| Upward Gaze | | | | | | | | | | | | | | |
| RtWard Gaze | | | | | | | | | | | | | | |
| LtWard Gaze | | | | | | | | | | | | | | |
| UpLeft Gaze | | | | | | | | | | | | | | |
| DownLeft Gaze | | | | | | | | | | | | | | |
| UpRight Gaze | | | | | | | | | | | | | | |
| DownRight Gaze | | | | | | | | | | | | | | |

Computerized Dynamic Posturograpy

Notes:

*FIG. 6*

METHOD FOR DIAGNOSIS OF AND THERAPY FOR A SUBJECT HAVING A CENTRAL NERVOUS SYSTEM DISORDER

CROSS-REFERENCE TO RELATED APPLICATIONS

This application claims the benefit of U.S. Provisional Application No. 61/726,511, filed Nov. 14, 2012, the contents of which are incorporated herein by reference in their entirety.

TECHNICAL FIELD

The present invention relates to an apparatus and method for diagnosis of and therapy for a subject having a disorder of the central nervous system, and more particularly to providing CNS therapy through a judicious combination of a subject's posture and environmental stimuli.

BACKGROUND ART

It is known in the prior art that brain injury is one the leading causes of disability. In addition to the obvious, highly visible victims—returning soldiers and those who have suffered strokes—it is reported that a very high percentage of today's prison inmates have some form of brain injury related impairment. The advanced training and methods of first responders and emergency departments has led to a much greater rate of surviving a major traumatic head/brain injury. Adding to this population are children and young adults who have suffered sports related head injuries, as well as violence/abuse related brain injury. Another population affected by brain injury/dysfunction are those with developmental disorders and learning disabilities. Whether the etiology of this dysfunction is genetic, congenital or environmental, it still manifests an underlying brain function anomaly. These disorders can be comorbid with traumatically acquired brain injury and therefore greatly compound the overall impairment. Many of these injuries result in lasting changes in memory, computational, emotional, as well as autonomic function. It is reported that unemployment among this population is disproportionately high, and some find it impossible to maintain employment, even with placement, due to their cognitive impairments.

The diagnosis and treatment of brain-based lesions have been extremely dependent upon the geographic location and the particular facility within that location where treatment is sought. The choice of intervention and which treatment protocols that are followed are based largely upon the traditions and practices of the particular therapists and doctors who compose the patient's treatment team. Frequently in these cases, only the life threatening aspects of the disorder/injury are addressed, neglecting soft or 'functional/ physiological' lesions, even if an extensive rehabilitation regimen is undertaken. It is a widely held belief in social work, cognitive rehabilitation and nutritional counseling, but not consistently implemented, that—once stabilization has occurred following post-neurosurgical, traumatic, acquired brain injury, or even developmental, disorders and learning difficulties have manifested—therapy directed at producing lasting change to the structural and functional integration should be a major portion of any rehabilitation process.

Moreover, there is a functional and spatial mapping between different areas of the brain and different areas of the body. For example, the body includes afferent nerves that carry sensory signals to the central nervous system, including the state of smooth muscle contraction in arteries, the amount of local blood flow to an area, local temperature, the presence of chemistry related to tissue injury, and pH, $O_2$, and $CO_2$ levels. By contrast, efferent nerves carry motor signals from the central nervous system to the muscles. These two types of nerves serve different purposes, and are located in different places within the brain. Injuries to different parts of the brain therefore sometimes manifest themselves as dysfunction of different areas of the body, either as diminished sensory capability or as diminished motor capability.

Small diameter afferent fibers consist of Type C and A$\delta$ peripheral nerve fibers. These are thin, unmyelinated, and slow conducting in nature. The information they relay includes the state of smooth muscle contraction in arteries, the amount of local blood flow to an area, local temperature, the presence of chemistry related to tissue injury, and pH, $O_2$, and $CO_2$ levels. Type 2 C fibers are strongly activated by non-painful cold and heat stimulation. These fibers converge onto the VMpo thalamic nucleus, and by way of the NTS and PB (Parabrachial) nucleus, onto the VMb thalamic nucleus. The VMpo thalamic nucleus fibers connect onto the anterior and posterior insular neural maps. Fibers from the VMb thalamic nucleus synapse onto the posterior insular cortex.

Using traditional treatment methods for chronic pain have had poor outcomes, especially if the pain is caused by a sympathetic nervous system disorder that can be exacerbated by a wide variety of unrelated triggers such as food and weather. Some individuals may simply cope with the pain, traveling from doctor to doctor, never getting an accurate diagnosis, being told that their pain is "all in their head". One such disorder is reflex sympathetic dystrophy (RSD) syndrome, also known as complex regional pain syndrome (CRPS). RSD has no known cause and no known cure.

SUMMARY OF THE EMBODIMENTS

Various embodiments of the invention described herein recognize that different body postures affect the autonomic nervous system differently, and therefore various external stimuli may have different therapeutic efficacies when a patient or subject is in each body posture. Postures, such as walking, sitting, standing, and supine, have different effects on the autonomic nervous system, and therefore some stimuli have different physiological efficacies while a patient or subject is in a given body posture. Disclosed embodiments of the present invention leverage this relationship to determine a combination of posture and stimulus that has optimal therapeutic effect. These embodiments provide a treatment that stimulates the nervous system through a combination of noninvasive therapies that stimulate brain cells to increase their efficiency—this promotes the formation of pathways that help transfer information throughout the brain in such a way that in the end, the affected area of the brain and overall brain function are improved without medication or surgery. Indeed, the autonomic response advantageously may be addressed as the first step in the examination and rehabilitation process. It is further noted that, while a treatment may alleviate some symptoms of an underlying disability or illness, such as complex regional pain or RSD, it might not cure all the causes of the illness. Further embodiments thus provide for reevaluating the optimality of the posture/stimulus combination once relative normalcy has been achieved with respect to a given monitored physiological response, to determine whether any residual dysregulation remains.

In accordance with an embodiment of the invention, there is provided a method of systematically evaluating dynamic autonomic dysregulation in a subject. The method includes having the subject sequentially assume a plurality of distinct postures that may include, for example, walking, standing, sitting or supine. In each posture of the subject, the subject is subjected to sensory stimulation while measuring at least one autonomic physiological response of the subject. The autonomic physiological response may include, for example, oxygen saturation, heart rate, pupillary response, blood pressure, sweat production, pseudomotor activity or respiration. The physiological responses in each of the distinct postures are evaluated to identify a posture wherein the subject exhibits a least amount of dysfunction.

In accordance with related embodiments of the invention, subjecting the subject to sensory stimulation may include subjecting the subject to a stimulus selected from the stimulus group consisting of TENS, non-painful heat, non-painful cold, visual, occulomotor stimulation, crude touch, olfactory stimulation, vestibular stimulation, and auditory stimulation. At least one parameter of the stimulus may be varied while subjecting the patient to the stimulus. For example, the amplitude, frequency, and/or duration of the stimulus may be varied.

In accordance with further embodiments of the invention, subjecting the subject to sensory stimulation may include sequentially subjecting the subject to a plurality of stimuli selected from the stimulus group, the method further including evaluating the physiological responses to the stimuli at the identified posture to identify a stimulus that provides an optimal physiological response by the subject. The physiological responses to the identified stimulus at the identified posture may be evaluated to identify a parameter value that provides an optimal physiological response by the subject.

In accordance with further related embodiments of the invention, the subject may be treated, for example, by subjecting the subject to the identified stimulus while the subject is in the identified posture. The subject may be repeatedly subjected to the identified stimulus, while the subject is in the identified posture, until a desired endpoint physiological condition is achieved. The desired endpoint physiological condition may be a condition wherein subjecting the subject to a stimulus from the stimulus group, other than the identified stimulus, does not cause dysfunction in the subject while the subject is in the identified posture.

In accordance with still further related embodiments of the invention, upon achieving the desired endpoint physiological condition, the method may include, for at least one posture different from the identified posture, determining whether a dysfunction in the subject exists upon subjecting the subject to a stimulus selected from the stimulus group. Upon existence of a dysfunction, the subject may be repeatedly subjected to a stimulus selected from the stimulus group at the different posture until a further desired endpoint physiological condition is achieved. If no dysfunction in the subject exists while the subject is in the at least one posture different from the identified posture, the method may further include performing additional therapeutic modalities to facilitate further enhancement of physiological condition.

In accordance with another embodiment of the invention, there is provided a method for providing therapy using afferent nerve pathways for a subject having a brain disorder, the subject having a body. The method includes providing a stimulus to the subject, over selected portions of the body of the subject. The stimulus may include TENS, non-painful heat, non-painful cold, visual, occulomotor stimulation, vestibular stimulation or crude touch. Response of the subject to the stimulus is monitored with respect to at least one autonomic physiological response of the subject. The autonomic physiological response may include oxygen saturation, heart rate, pupillary response, blood pressure, sweat production, pseudomotor activity or respiration. At least one stimulus parameter is adjusted, such as selection, intensity, location, and duration of the stimulus, so as to cause a change in the monitored response in a direction toward normal, while limiting stimulus parameters so that the stimulus is tolerated by the subject.

In accordance with related embodiments of the invention, the method may include simultaneously or consecutively providing to the subject an additional therapeutic regime. The method may further include repeating, at different distinct postures, providing a stimulus, monitoring response, and adjusting at least one stimulus parameter. The distinct postures may include walking, standing, sitting, and supine.

BRIEF DESCRIPTION OF THE DRAWINGS

The foregoing features of embodiments will be more readily understood by reference to the following detailed description, taken with reference to the accompanying drawings, in which:

FIG. 5 is an exemplary patient log for use by a physician during treatment of an illness according to an embodiment of the invention; and FIG. 6 is another exemplary patient log for use by a physician during treatment of the illness.

DETAILED DESCRIPTION OF SPECIFIC EMBODIMENTS

Figure 1:
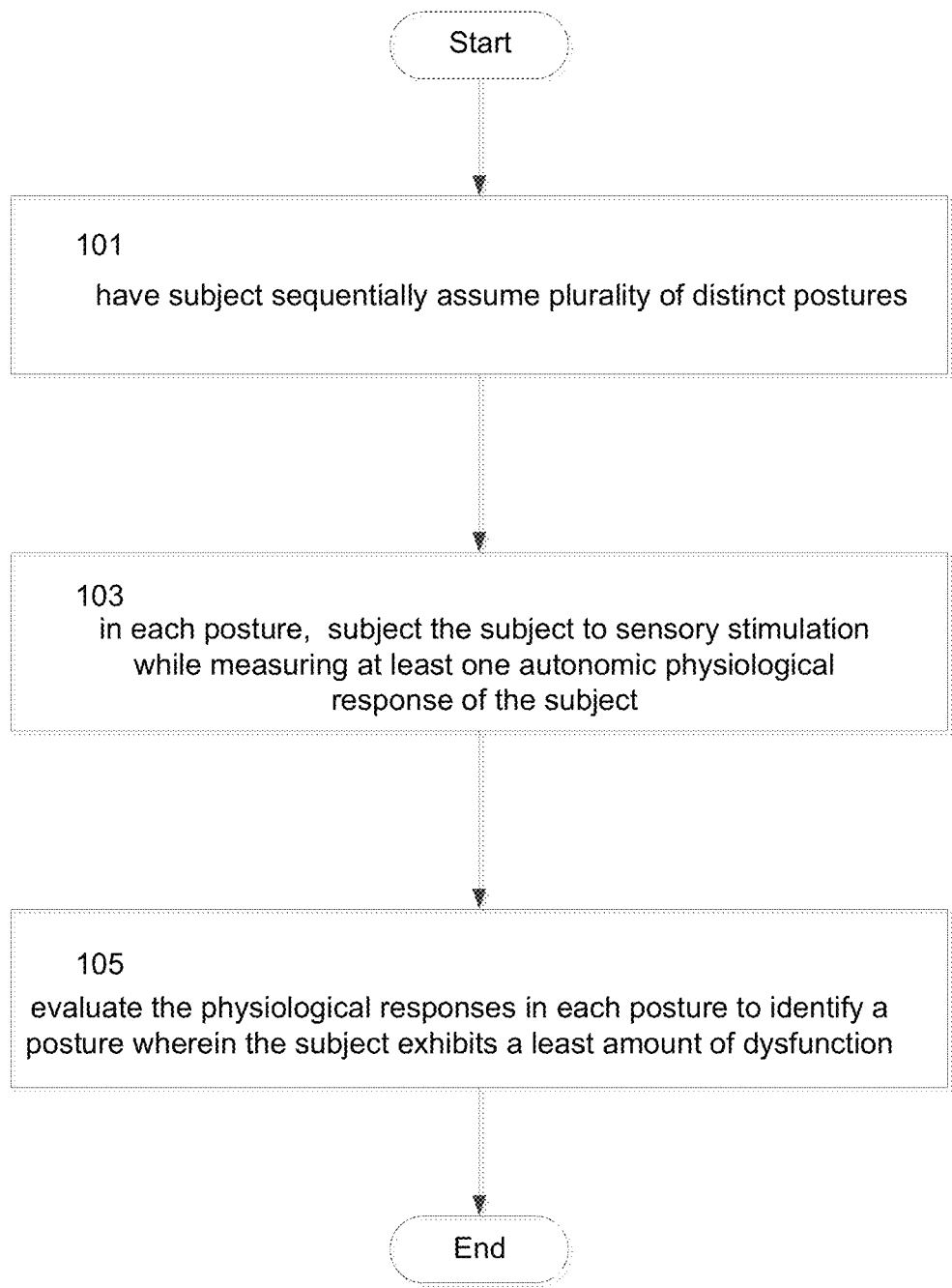
FIG. 1 is a flowchart showing a method in accordance with an embodiment of the invention.

Various embodiments of the invention described herein produce lasting change by incorporating different combinations of posture and environmental stimuli into the therapeutic regimen. Postures, such as walking, sitting, standing, and supine, have different effects on the autonomic nervous system, and therefore some stimuli have different physiological efficacies while a patient or subject is in each body position. Disclosed embodiments of the present invention leverage this relationship to determine a combination of posture and stimulus that has optimal therapeutic effect. These embodiments provide a treatment that stimulates the nervous system through a combination of noninvasive therapies that stimulate brain cells to increase their efficiency—this promotes the formation of pathways that help transfer information throughout the brain in such a way that in the end, the affected area of the brain and overall brain function are improved without medication or surgery. Indeed, the autonomic response advantageously may be addressed as the first step in the examination and rehabilitation process. Moreover, while a treatment may alleviate some symptoms of an underlying disability or illness, it might not cure all the causes of the illness. Thus, further embodiments provide for reevaluating the optimality of the posture/stimulus combination once relative normalcy has been achieved with respect to a given monitored physiological response, to determine whether any residual dysregulation remains.

The methods disclosed herein address one of the main problems inherent in injured or dysfunctional neurological tissue—that of fragility of the supporting structures, and insufficient ability to supply adequate fuel needed for the increased metabolic activity for repair of the damaged areas. This differs from prior approaches of non-emergent brain injury treatment which generally employed a strategy of doing nothing or of prescribing "rest". The disclosed methods, by employing the following steps, have succeeded in the goal of providing for a greater survivability and favorable outcome of the neurological rehabilitation and recovery process.

As used in this description and the accompanying claims, the following terms shall have the meanings indicated, unless the context otherwise requires:

The "labyrinthine system" is the sensory system of the inner ear that contributes to movement and balance. It has two components: the semicircular canal system, which indicates rotational accelerations, and the otoliths, which indicate linear accelerations. The labyrinthine system signals to both the neural structures that control eye movements and to the muscles that control posture. The labyrinthine system is part of the vestibular system, whose primary purpose is to detect the motion of the head and then generate reflexes that stabilize gaze and maintain the body's posture in gravity.

The "vestibulo-ocular reflex" or "VOR" is a reflex eye movement that stabilizes images on the retina during head movement by producing an eye movement in a direction opposite to the head movement. Since slight head movement is present at all times, the vestibulo-ocular reflex is essential for stabilizing vision.

"Smooth pursuit" refers to eye movements made while closely following or tracking a moving target. By contrast, "saccades" are rapid, simultaneous movements of both eyes in the same direction that redirect the line of sight.

"Computerized tracking tests", as defined herein, are clinical tests that measure a patient's ability to match eye movements to visual target movements. Such clinical tests can be utilized to identify and diagnose disturbances in the central nervous system.

"Video electronystagmography", or "VENG" is a comprehensive evaluation of the oculomotor and vestibular systems comprised of computerized tracking tests (smooth pursuits and saccades) and optokinetic nystagmus ("OKN"). The VENG evaluation can be used to detect involuntary movements of the eye caused by nystagmus. As part of the VENG evaluation, patients are typically fitted with lightweight goggles that house infrared cameras. The cameras track and record eye movements and pupillary responses to visual targets. When the test begins, patients are asked to match their eye movements to those visual targets (i.e. lines, dots, etc.) that are projected onto an LCD screen in front of them (which may be provided using headgear approximately 2" away from the patient, or using a wall-mounted screen up to approximately 72" away from the patient). Tests typically range from 30-60 seconds, with varied target velocity, acceleration, and frequency. Throughout each test, computerized software measures the patient's overall accuracy and response time. For example, in some cases, the eye falls behind the target and has to make abrupt rapid movements to catch up (known as the "catch-up saccade"). At other times, the patient may be going faster than the target in anticipation of the next movement. Either response may reflect a disturbance in the central nervous system.

"Computerized dynamic posturography" or "CDP" is a non-invasive test of balance used to assess the central nervous system mechanisms involved in the control of posture and balance. Generally, CDP is carried out by placing a patient in standing posture on a fixed instrumented platform (force plate) with or without perturbing cushion. The platform is connected to sensitive detectors (force and movement transducers) that detect subtle oscillations of the body. Tests typically span 20 seconds with varied movements and head positions (i.e. neutral, left rotation, right rotation, flexion, extension, downward gaze). CDP produces graphic metrics that identify minute spontaneous body sways and overall balance scores. Abnormalities or below-average scores may reflect impairments in the central nervous system ("CNS") that affect the posture control system.

A "caloric test" is a thermal test of the lateral semicircular canals that is used to identify disorders of the inner ear and/or to detect bilateral weakness of the brain. The standard bithermal caloric test may be performed on patients by irrigating warm and cold water into each ear sequentially. During the procedure, the patient is seated, with head inclined 30 degrees up from horizontal to ensure that the lateral canal is horizontal. Warm water is then slowly inserted into the ear canal on one side, using a large plastic syringe. The water is stopped after 30 seconds, and spontaneous nystagmus is observed. After a rest of approximately 5 minutes, the test is repeated on the other side. If no response is detected, the test is repeated using cold water.

Temperature change can be manipulated to stabilize a patient's autonomic functioning. In a typical "temperature test", the patient lies horizontally on a bench. To dampen all forms of stimulation, the lights are darkened, and the patient is offered ear plugs and red tinted glasses. Warm towels are then applied to the upper and lower extremities (specific side to be determined by the attending physician). After approximately 5-7 minutes, the towels are replaced with new, warm water. This process trains the autonomic system to withstand environmental and physiological changes, thereby stimulating small diameter afferents to elicit autonomic responses.

"Chair rotation with visual fixation" is a test used to identify the presence of a central (cerebellar or brainstem) lesion. For this diagnostic test, the patient is seated upright in a rotating chair and asked to fix his/her eyes on a clearly visible target. Typically, the patient holds a pen in his/her hand and focuses his/her gaze on the tip of that pen. The patient is then spun slowly in either direction (to be determined by the attending physician based upon the cerebellar deficit) in quarter turns. Throughout this exercise, the physician observes the adequacy of gaze holding. Impaired gaze holding, or a drift of the eye in a certain direction, may indicate the presence of a lesion. Additionally, this exercise is utilized as a therapeutic modality to train the cerebellum and frontal lobe to suppress the nystagmus reflex that occurs during rotation.

"Transcutaneous electrical nerve stimulation" or "TENS" is a non-invasive, low-risk form of nerve excitation used to reduce acute and chronic pain and/or myospasm. A portable TENS unit is typically applied directly to the skin using two or more electrodes. The standard battery-operated TENS unit modulates pulse width, frequency, and/or intensity.

"Gait" means a manner of walking.

"Brain timing and sequencing" refers to a computerized evaluation that identifies the motoric system's processing speed in executing complex motor commands in response to a generated auditory cue. Temporal differences between the auditory cue and the patient's performance are measured in milliseconds, reflecting the patient's overall processing speed. To strengthen brain timing and sequencing, the complex motor commands-including hand and foot exercises-are repeated as therapeutic activities once treatment progresses.

"Stimulation" or "sensory stimulation" means any form of sensory modality that is used for diagnosis or treatment of a disease, and includes visual stimulation, auditory stimulation, occulomotor stimulation, olfactory stimulation, vestibular stimulation, vibratory stimulation, caloric stimulation, temperature-change stimulation, TENS, non-painful heat, non-painful cold, and crude touch.

"Subject" or "patient" means an individual being treated for an illness.

"Illness" means an illness of a human being, and includes, among other things, migraine, reflex sympathetic dystrophy (RSD) syndrome or complex regional pain syndrome (CRPS), postural orthostatic tachycardia syndrome (POTS), concussion, traumatic brain injury (TBI), apraxia, apraxia of speech, aphasia, cervicogenic dizziness, migraine-associated vertigo, vestibular illnesses, attention deficit hyperactivity disorder (ADHD), autism, Asperger Syndrome, fibromyalgia, chronic fatigue, mal de débarquement syndrome (MdDS), multiple sclerosis (MS), Parkinson's disease, restless leg syndrome (RLS), insomnia, dysautonomias, peripheral nerve injuries, tremors, ataxia, asthma, and sciatica.

A summary of investigations into eye movements, their role in understanding brain function, and their use in diagnosis of neurological conditions can be found in a primer on visual neuroscience, entitled "Neuroscience of Eye Movements" by R. John Leigh, MD, FRCP and Sangeeta Khanna, MD, published by ACNR, VOLUME 5 NUMBER 6 JANUARY/FEBRUARY 2006. This paper as well as the book it references, Leigh R J, Zee D S, The Neurology of Eye Movements (Book/DVD), Fourth Edition, 4 ed. New York: Oxford University Press, 2006, are hereby incorporated herein by reference. In summary, this paper states that an understanding of normal eye movements, and knowledge of their biological substrate, purpose and properties will greatly assist in determining the location of a neurological lesion. Dr. Leigh asserts that most diseases that affect the brain have, to some degree, an effect on eye movements.

FIG. 1 is a flowchart showing a method for evaluating dynamic autonomic dysregulation in a subject in accordance with an embodiment of the invention. In a first process 101, a patient or subject is directed to sequentially assume a plurality of distinct postures. These postures may include, for example: standing, sitting, supine, and/or walking.

In a second process 103, in each of the assumed body positions, the patient or subject is subjected to sensory stimulation while at least one autonomic physiological response is simultaneously measured. In an exemplary embodiment, the patient is examined using a pulse oximeter in each of these positions to measure blood oxygen saturation; however, other physiological responses such as heart rate, pupillary response, blood pressure, sweat production, pseudomotor activity, and respiration also may be measured in accordance with various embodiments.

An exemplary process 103 is now described in more detail. First, a physician may direct the patient to stand, and place the pulse oximeter on one of their fingers. Next, the physician takes an initial reading with the patient standing with their head facing forward and their eyes open. Next, the physician moves the patient's head into each canal position (left horizontal rotation, right horizontal rotation, left posterior extension, right anterior flexion, right posterior extension, and left anterior flexion) with the patient's eyes remaining open. After placing the patient's head in the each of the canal positions, the physician takes and records pulse oximeter readings while having the patient place their visual axis in a neutral position, then in ipsilateral gaze, then in contralateral gaze. The head positioning procedure and readings are repeated with the patient's eyes closed. This overall procedure is repeated with the patient sitting, then lying supine. Finally, a recording is taken with the patient walking briskly.

While the stimulation described above involves repositioning of the ear canals through head movement and adjusting the patient's gaze, other sensory stimulation may include, for example, visual stimulation (e.g., quadrantinopial and hemianopial stimulation) and auditory stimulation (e.g., a pitch changing from a low frequency to a high frequency). If the subject is sitting in a chair, sensory stimulation may include chair rotation with head fixed and with or without visual fixation. Other sensory stimulation could include efferent copy stimulation, such as requiring the subject to perform motor tasks. Still other sensory stimulation includes vibratory stimulation, gyroscopic stimulation, temperature change stimulation, and TENS. The stimulations of process 103 may be chosen to differentiate between the various components of the vestibular system, including the visual component, the labyrinthine component, the spinal component, and the cortical component. The process 103 aids in determining the competent stimulation that will be used for treatment.

In a third process 105, the physiological responses for each posture are evaluated to identify a posture wherein the patient or subject exhibits a least amount of dysfunction. The physiological responses for each posture may be assigned a score based on the amount of dysregulation indicated, for example, and these scores may be combined to form a score for each posture that represents the overall amount of dysfunction. At this time, a body posture of greatest dysfunction may be determined to use as a baseline against which to measure the efficacy of the treatment regimen. If the posture is recumbent, then the patient's sensory stimulation tolerance needs to be determined by performing a further battery of tests using the above-described stimuli. These sensory stimuli are provided with respect to both the left cortex of the brain and the right cortex of the brain to identify whether the measured physiological response indicates an increased or decreased dysregulation (i.e., a further or closer distance from a normal value), and act as a confirmation of the competent stimulation.

At some time during the examination, the physician may employ computerized dynamic posturography to confirm various properties of the injury or illness, such as a lesion's side and level diagnosis for example. Thus, for example, the physician may direct the patient to stand with their eyes closed and record a stability score and fatigability ratio for each of the following positions: head facing forward, head turned leftward, head turned rightward, head down-rightward, head back-leftward, head down-leftward, and head back-rightward. The physician may then repeat the procedure for autonomic stressors. Also, the physician may perform a VENG examination to set a baseline for the autonomic subsystems, and perform a pupillometry examination to confirm changes to the baseline.

It should be understood by one skilled in the art, that many other combinations of stimuli, different monitoring windows, and examination order or operation may be employed.

Figure 2:
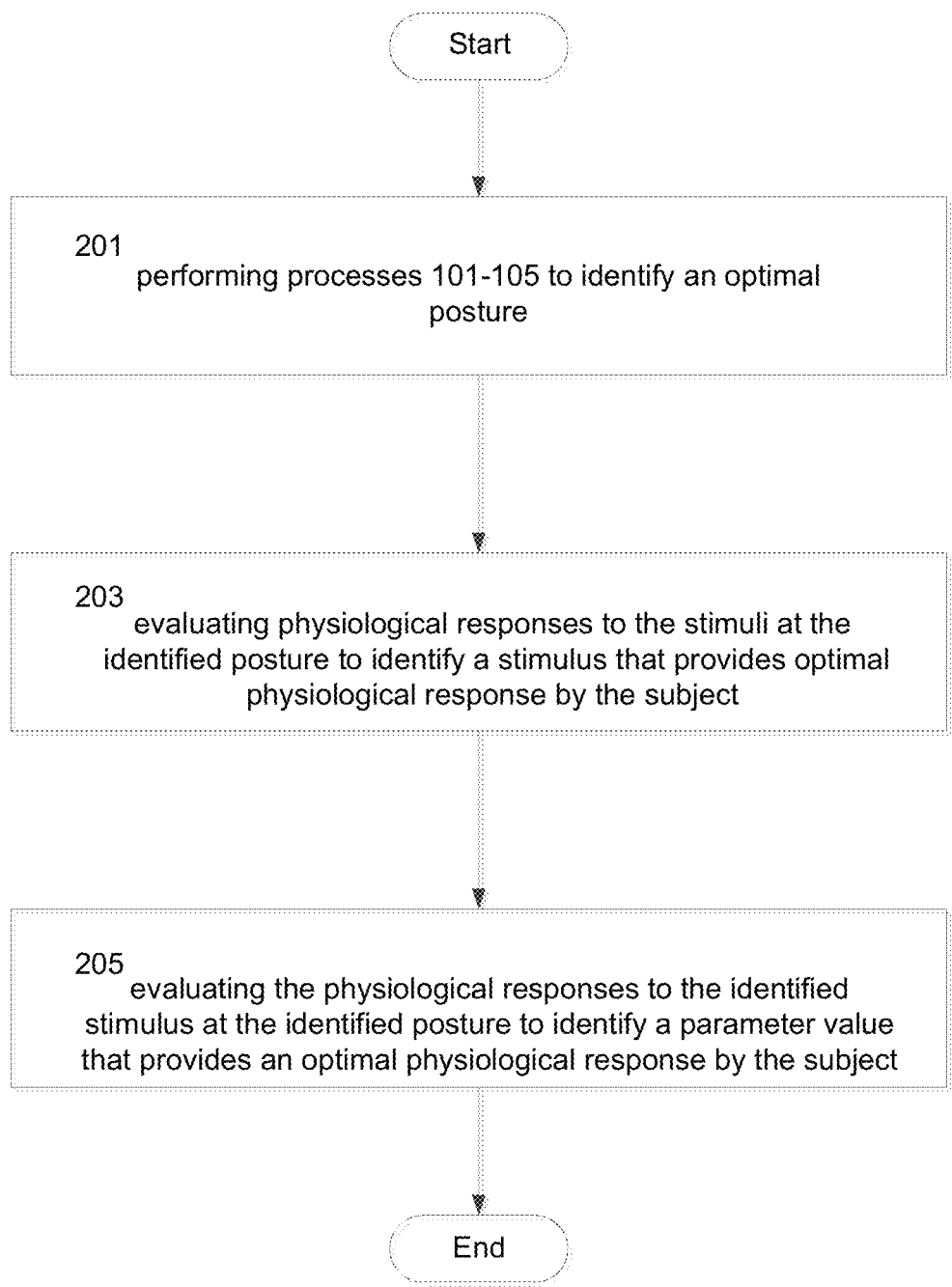
FIG. 2 is a flowchart showing a method in accordance with a further embodiment of the invention.

FIG. 2 is a flowchart showing a method in accordance with a further embodiment of the invention. Process 201 simply requires performing the processes of FIG. 1 to identify an optimal posture. Process 203 requires evaluating physiological responses to the stimuli at the identified posture to identify a particular stimulus that provides optimal physiological response by the subject while in that posture. Thus, while process 105 identifies an optimal posture for treatment as a function of a variety of stimuli, process 203 identifies the best stimulus for the optimal posture.

Process 205 fine-tunes the treatment regiment by evaluating the physiological responses to the identified stimulus at the identified posture, to identify one or more parameter values that provide an optimal physiological response by the subject. Thus, if the processes 101 to 203 identify auditory stimulation in a supine position as the most efficacious treatment, process 205 would determine, for example, a duration, amplitude, and frequency of the auditory stimulation that produces the least dysfunction. Other combinations of posture and stimulus require optimization of other parameters, as should be apparent to a person having ordinary skill in the art.

Once these processes 101-205 are complete, a treatment strategy may be determined. Such a strategy is a function of at least four elements. The first element is the posture of least dysregulation, which is used to determine a best posture for treatment. The second element is a ranking of stimulation modalities in terms of their effectiveness of physiological response, with the optimal modality being preferred. The third element is the quality of the motor response to the competent stimulus, which is used to determine the duration, amplitude, and frequency of the optimal stimulation. The fourth element is the collection of sensory modalities or stimulations which drive the vital centers toward normalized physiology or normal autonomic windows, as these adaptive competent stimulations are capable of producing adaptive neuroplasticity, and therefore promote system integrity and function. Other elements may be considered in determining the treatment strategy, if deemed relevant by the physician.

Figure 3:
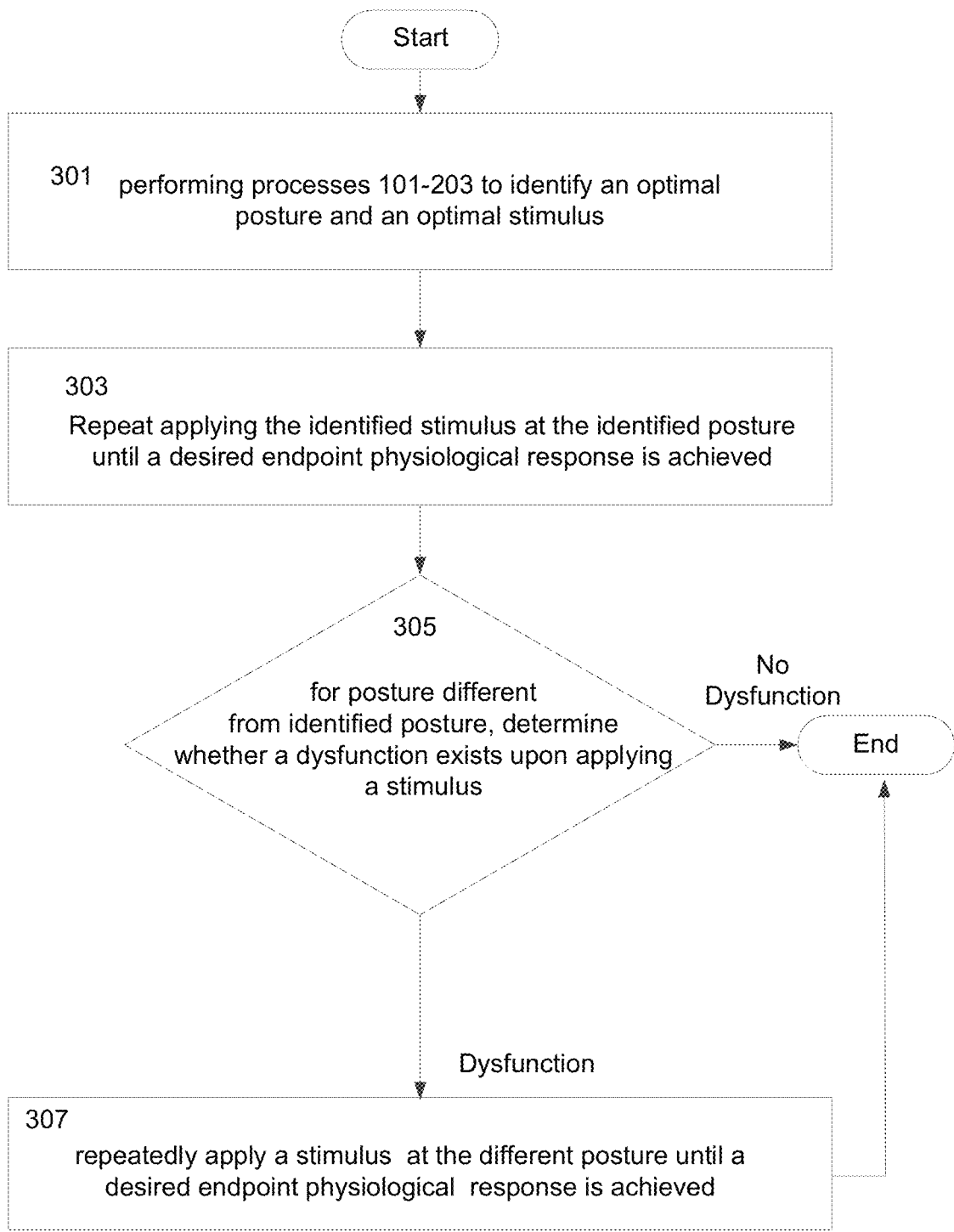
FIG. 3 is a flowchart showing a method in accordance with another further embodiment of the invention.

In some situations, when a desired endpoint physiological condition is reached, subjecting the patient to a stimulus other than the identified optimal stimulus does not cause dysfunction while the subject is in the identified posture. In such situations, the patient may be approaching a state of physiological normalcy. However, even if a patient is treated according to an optimal posture and an optimal stimulus until that patient shows relative normalcy, it may be that the particular treatment regiment has addressed only one observed symptom of the underlying illness, and other stimuli may cause reactions indicative of continued dysfunction. FIG. 3 is a flowchart showing a method in accordance with another further embodiment of the invention that detects this situation and rectifies it.

Process 301 simply requires performing the processes 101-203 to identify an optimal posture and an optimal stimulus. The next process 303 calls for repeatedly applying the identified stimulus to the subject at the identified posture until a desired endpoint physiological response is achieved. However, once a normal response is observed for this first posture, process 305 determines, for a posture different from the first posture, whether a dysfunction exists upon applying a stimulus. It should be noted that the stimulus applied need not be the identified optimal stimulus, but may be any appropriate stimulus as described above, and that the dysfunction need not be the dysfunction identified during the diagnostic processes 101-105. If the process 305 determines that there is no dysfunction, then the treatment is considered successful and may end as indicated in FIG. 3. However, if the process 305 determines that a dysfunction is still present, then in process 307, the physician repeatedly applies a stimulus at the different posture until a desired endpoint physiological response is achieved. Thus, the physician may repeat the processes 201-205 to determine the optimal stimuli for the new posture, and apply process 303. If required, the treatment regimen may require several such applications and visiting a posture several times until normalcy is attained. The physician may track the patient's physiological reactions in the various postures using a patient log, for example a log of vital signs as reproduced in FIG. 5, and may correlate this information against the effects of various stimuli on the patient's posture control, as recorded in a CDP log such as the one reproduced in FIG. 6.

The above embodiments of the invention are directed to the advantages of the use of different postures in treating illnesses. Some of these stimuli cause physiological reactions that operate on efferent nerves—the nerve fibers that carry signals away from the CNS toward the motor system to cause movement. For example, intentional eye movements may be an effective diagnostic tool if the efferent nerves that carry electrochemical signals from the brain to the ocular muscles are functioning properly. However, such intentional movements may not occur if the CNS does not receive the stimuli in the first place. Such non-reception may be due to damage of the afferent nerve fibers—the nerve fibers that carry stimuli from receptors or sense organs toward the CNS.

In subjects with localized damage or loss of the afferent nerves, some stimuli such as pain, heat, itchiness, pressure, and sense of touch that originate in those damaged areas will not reach the CNS. This may occur, for example, in subjects who have lost limbs or suffered severe burns. For these subjects, the processes described above may be ineffective on certain areas of the body, but effective in other areas that have functioning afferent nerves.

Figure 4:
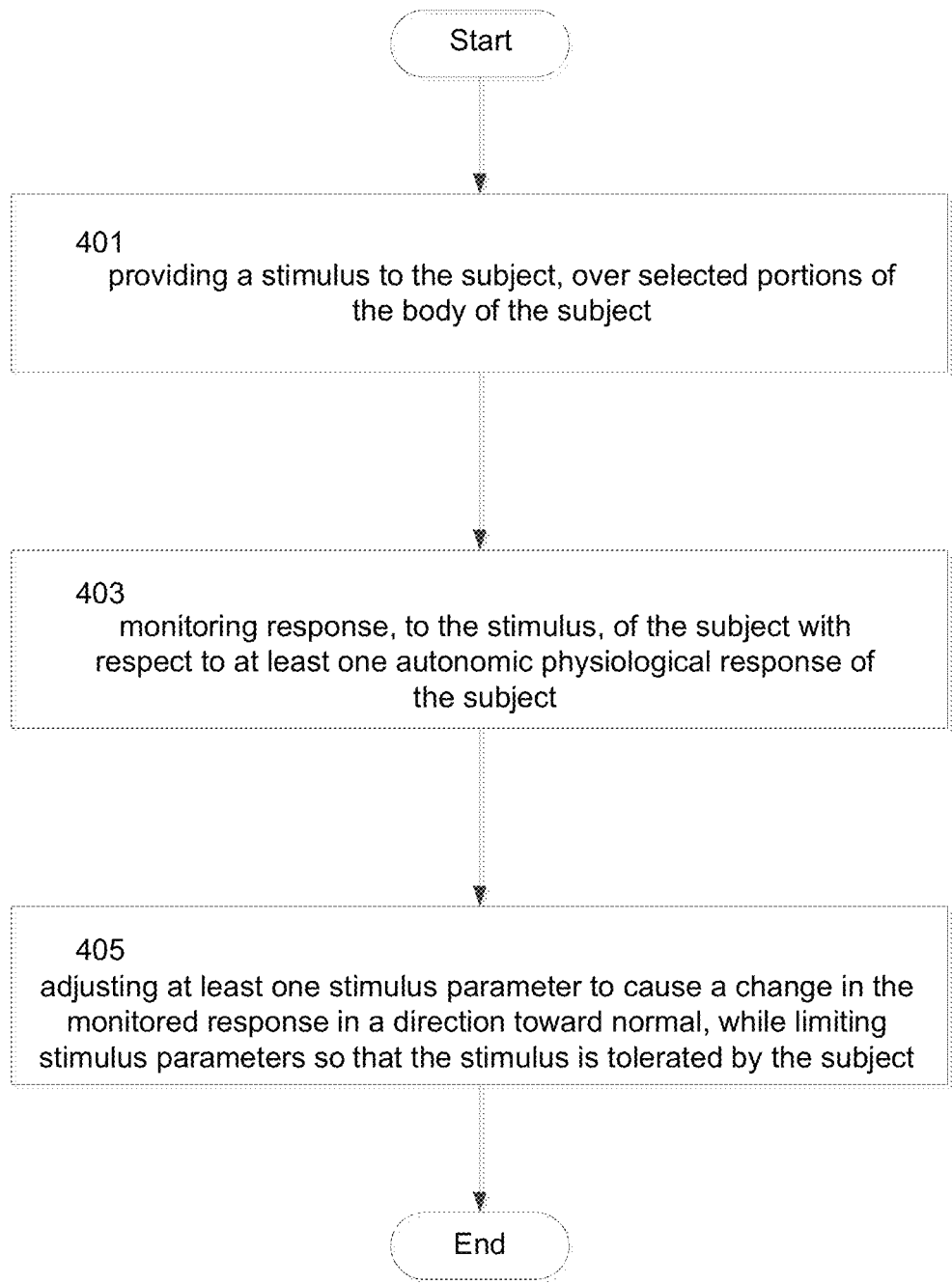
FIG. 4 is a flowchart showing a method in accordance with another embodiment of the invention.

FIG. 4 is a flowchart showing a method in accordance with another embodiment of the invention. This method provides therapy using different afferent nerve pathways for a subject having a brain disorder. In a first process 401, a physician provides a stimulus to the subject over selected portions of the subject's body. As described above, these stimuli may include TENS, non-painful heat, non-painful cold, visual stimuli, auditory stimuli, occulomotor stimuli, vestibular stimuli, crude touch, or any other stimuli herein disclosed. In a next process 403, the physician monitors the response of the subject to the stimuli with respect to at least one autonomic physiological response. This process is similar to process 103, except that the diagnostic variable is body location rather than body posture or orientation. In particular, the measured autonomic physiological response may be blood oxygen saturation, heart rate, pupillary response, blood pressure, sweat production, pseudomotor activity, or respiration. In a further process 405, the physician adjusts at least one stimulus parameter to cause a change in the monitored response in a direction toward normal, while limiting stimulus parameters so that the stimulus is tolerated by the subject. The adjusted parameter(s) may be, for example, selection, intensity, location, or duration of the stimulus.

In accordance with the embodiment of FIG. 4, the physician may simultaneously or consecutively provide an additional therapeutic regime to the subject to promote better healing. Moreover, the teachings of the embodiments of FIGS. 1-3 may be combined with the embodiment of FIG. 4, so that once a suitable body location is found for application of stimuli, these stimuli may be applied to that body location as autonomic physiological responses measured and recorded, while the patient assumes a variety of postures (e.g., walking, standing, sitting, and supine).

Successful Treatment Example: Post-Concussion Syndrome

A 25 year old female presented for Cortical Integrative Therapy ("CIT") evaluation and treatment of symptoms related to a mild traumatic brain injury, post-concussion syndrome (PCS), subsequent to a sports related head injury that resulted in concussions 8 years prior. The concussion occurred while she was participating in a high school basketball game.

After seeing approximately 80 physicians and therapists the patient continued to experience many residual symptoms from her head injury; headaches, dizziness, neck pain, stiff neck nervousness, fatigue, irritability, cold sweats, and her eyes having an excessive sensitivity to light. Her daily headaches continued (pain rated at 4-5 out of 10), and she continued with difficulty with focus and concentration. The patient reported never having these issues prior to the head traumas and now her current symptoms were interfering with her routine activities of daily living, including; her job, schooling, and sleep. She reported that reading, bright lights, and tasks that require concentration/focusing were what tend to aggravate her symptoms the most. The patient described light headedness daily, usually for bouts of about 10 minutes at a time. These episodes were accompanied by her vision getting blurry and the sensation she was going to fall over, although she never fell. She also described "her eyes blacking out", which occurred occasionally when she stood up rapidly. Doing so would cause her to lose her vision until she bent down, but this would cause nose bleeds, limiting her strategy to abate the visual disturbance. Additionally, the patient reported "jaw issues" subsequent to her head trauma as she sustained torn cartilage in her TMJ. This appeared to be a contributing factor in her headaches.

The patient reported that her initial symptoms (severe migraines, nausea, trouble with focus and concentration, and major balance problems) were addressed by at least three different hospitals. Most of the care consisted of pain medications and antidepressants. She received intensive physical therapy to help her to learn how to walk without falling over. The patient reported she followed this care plan for four years without much benefit.

The patient subsequently was referred to another hospital, where she reported being admitted for approximately 8 days on two separate occasions. These hospital stays consisted of high powered pharmaceutical interventions, including fentanyl patches, other narcotics, and Botox injections, attempting to treat her migraines. Unfortunately, these treatments had little to no benefit. Acupuncture and traditional Chinese medicine appeared to greatly decrease the number of migraines she suffered to just "severe" headaches. This change permitted the patient to attempt taking some college classes. In the semester prior to seeking care at this office, she took three online courses. She would be able to read for 20 minutes at a time, but would then have to go lie down and close her eyes. The patient reported increased headaches, difficulty remembering what she was learning and was easily distracted. She reported that doing homework was akin to "the feeling of having finished running a marathon and then getting a headache". The patient reported feeling that she was going backwards, and it was scaring her into seeking further evaluation and treatment.

CIT treatment began Jan. 7, 2013. During the evaluation process, a TENS unit was placed on different areas of her body. When it was placed on her left lower extremity it produced good stabilization of her heart rate, monitored by pulse oximeter: lying down the PO2 reading was 97 with heart rate 51 beats per minute, sitting the reading was 97 with heart rate 58 BPM, standing the reading was 99 with heart rate 73 BPM but with swings in heart rate in excess of 25 BPM at rest, bilaterally. The dysregulation was least while lying down, so her selected position for treatment was determined to be recumbent.

The patient was seen twice daily for 60 minutes where she was treated in a darkened environment and received application of warm moist towels, and a TENS unit on the right side. Over six treatment days, the swings in dysregulation narrowed over time to 1-5 BPM during head maneuvering.

After this, the patient graduated to the seated position where the process was repeated for three days, at which point she was able to sustain head movements, pursuits and optokinetic nystagmus (OKN) with 3-5 BPM variations. The patient then graduated to having the same regime applied while standing. On her tenth visit, we commenced adding additional modalities while her injury was treated as a left hemisphericity/right cerebellar diaschisis. The following additional modalities were performed daily over the course of the following six weeks were:

1. Left pursuits which are performed at 0.3 Hz, for 30 seconds.
2. Right lower quadrantinopial stimulation at a frequency of 0.3 Hz red/green checkered pattern for 30 seconds.
3. Right upper quadrantinopial stimulation at a frequency of 0.3 Hz red/green checkered pattern for 30 seconds.
4. Right Hemianopial stimulation at a frequency of 0.3 Hz red/green checkered pattern for 30 seconds.
5. Left OKAN performed at 0.3 Hz, for 30 seconds.
6. Right chair spin with visual fixation.
7. Right warm caloric treatment.
8. Spinal manipulation in coupled reduction to restore proper biomechanics and increase afferentation to the right cerebellum and left cortex.
9. Application of TENS unit for increased parietalization.

The visual and oculomotor activities were conducted in sets of 3 repetitions with 1 minute rest intervals. Treatment was performed within heart rate dynamic range below 95 BPM, with repetition and rest counts modified based on metabolic capacity. Treatment session time was 75 minutes.

By January 17th, we incorporated brain sequencing and timing activity in order to add movement parameters which were previously overwhelming. Continued repetition produced stabilization of autonomic regulation, permitting decrease in all symptoms and the improvement in her cognitive and overall functionality. The patient was discharged from active care on Mar. 4, 2013, at which time she returned to gainful employment and enrolled in Fall semester college classes.

Sample Therapeutic Regimen #1: RSD

Background: M. G., a 28-year-old female presents with reflex sympathetic dystrophy (RSD) in her right hand and wrist. Subsequent to sustaining a work-related injury, her right hand and wrist became excruciatingly painful. The pain resulted in a limited range of motion in her right shoulder, elbow and wrist due to the patient's attempt to protect her extremity from movement and from being touched by anything. Blood flow imaging demonstrated significantly decreased blood flow to the right forearm and particularly to the right wrist and hand. She also demonstrated limited movement of the cervical spine in rotation as well as extension. She initially forbade examination of her affected extremity due to excruciating pain.

Diagnosis: RSD (right hand and wrist) and decreased range of motion cervical spine in rotation and extension.

Typical office visit: The patient is greeted and escorted into the treatment room. Due to the patient's metabolic fragility, she is helped to lie down on the treatment table and the lights of the room are dimmed. Her pain on this day was listed at a 6 on a numerical pain rating scale 0 to 10 scale (0 being no pain, 10 being the most pain). A pulse oximeter is placed on her finger and used to measure the O2 saturation and heart rate. The initial readings are recorded, and the numbers are used to track and modify the therapeutic intervention choice, intensity and duration, so as to not exceed the patient's metabolic capacity during the activity. Her initial heart rate and O2 saturation are 92 beats per minute and 97% respectively. A warm moist cloth is placed on the patient's lower right leg, which is based upon favorable outcomes from last visit. The patient's heart rate lowers to 78 BPM and her O2 saturation is unchanged when the warm moist cloth is moved up to her superior medial knee area. The warm moist cloth is held at that location for two minutes, then the cloth is replaced with a fresh one to maintain the temperature level. The warm moist cloth is held at the location for a total of six minutes at two minute intervals. The heart rate stabilized to a range of 75 to 78 BPM. Her pain lowered to a 2 on the numerical pain rating scale.

The patient is then assisted to a seated position. After an initial fluctuation of her heart rate and PO2, it stabilizes back to the 75 to 78 BPM range. This is different than the previous visit in which she destabilized dramatically upon rising to a seated position from a supine position. Next, the patient remains seated and positioned so as to be able to view a projection screen, at a distance of about 72 inches. The patient is allowed to rest for one to three minutes while the next activity is set up.

Red tinted lens glasses are placed upon the patient, to lower the stimulation level. The warm moist cloth and pulse oximeter remain as prior, and Right Lower Quadrantinopial stimulation, displaying a red/green checkerboard pattern alternating at a 0.3 Hz for a duration of 30 seconds, is performed for six repetitions. The patient is instructed to fixate on the large red dot at the center of the screen while the checkerboards are flashing. The heart rate and PO2 are monitored and maintained at the 75 to 78 BPM range during the visual stimulation. The patient reports that her pain drops to 0 on the numerical pain rating scale. The patient is allowed to rest for one to three minutes in the darkened room. The treatment session's duration, including rest times needed, is 45 minutes.

The patient was scheduled to return the next day to continue with her prescribed treatment plan of a 2-week course of daily treatments, followed by a thorough reevaluation. The patient's cervical spine complaints was addressed when she became consistently, for 2 visits, without pain at the start of office visit.

Sample Therapeutic Regimen #2: RSD

Background: C. S., a 31-year-old female presents with RSD in both hands and arms. Her condition appeared as a result of chronic trauma and manifests as severe pain, weakness, and numbness of gradual onset, first in the right hand and arm then to include her left hand. Her left hand eventually became the area that was most symptomatic. A physician diagnosed carpal tunnel syndrome with flexor tendonitis. A surgeon operated on the patient's left wrist and trigger finger. Upon onset of occupational therapy, the patient began to experience increased pain, rating her pain at an 8 on a numerical pain rating scale 0 to 10 scale (0=no pain, 10=most pain), with hypersensitivity in the area of the scar, and decreased grip strength on either hand. Migraines and insomnia are concomitant to her main complaints. C. S. has a history of depression, anxiety, and memory difficulties.

Diagnosis: RSD (bilateral forearms and hands) and history of left wrist carpal tunnel surgery.

Typical Office Visit: The patient is greeted and escorted into the treatment room. On this day C. S. presented with her left hand pain significantly worse than her right hand. She rated her right hand pain at an 8 and her left at slightly less. She had additional symptoms of daily severe headaches, which she attributes to her lack of sleep. She rated her headaches at 9 on this day. She reported that her hands and feet sometimes felt abnormally cold to the touch. Despite her obvious pain, C. S. presented with a pleasant demeanor. A pulse oximeter is placed on her finger and used to measure the O2 saturation and heart rate. The initial readings are recorded, and the numbers are used to track and modify the therapeutic intervention choice, intensity and duration, so as to not exceed the patient's metabolic capacity during the activity.

A TENS unit is then fitted on the patient's left upper extremity, shoulder, and TMJ area, and she is seated in a chair about 72 inches from a projector screen. The room lights are lowered to facilitate better viewing. A left inferior quadrantanopial visual stimulation, consisting of red/green small checker squares is displayed with an alternating pattern at 0.3 Hz for a duration of 60 seconds, is performed for 6 repetitions. The patient is allowed to rest for one to three minutes in the darkened room.

Next, the patient is fitted with infrared camera goggles, generally used for VENG evaluations, which is used to monitor and record her eyes during the therapeutic pursuit eye movements, observing for breakdown of smooth movements. Six sets of rightward pursuits are performed at 0.3 Hz for 60 seconds, with a 60-second rest period between each set. Next, the patient is then escorted to a manual therapy room and is allowed to rest for one to three minutes.

Manipulation of the patient's thoracic spine and rib cage is performed to improve rib cage expansion, and therefore tidal volume. Her left shoulder is also manipulated to help normalize the overall muscle tone around her shoulder girdle. The patient is allowed to rest for one to three minutes in the darkened room.

C. S. tolerated the session well and reports a decrease in left hand pain to a 4, and her headaches were significantly improved. The treatment session's duration, including rest times needed, is 60 minutes. The patient is scheduled to return the next day to continue with her prescribed treatment plan of a 2-week course of 2 days-on-1 day-off office visits, followed by a thorough reevaluation.

Sample Therapeutic Regimen #3: RSD

Background: A. S., a 13-year-old male presents with a generalized RSD that causes severe to excruciating pain from the crown of his head to his buttocks and groin, with focal concentration targeting in the abdomen. He reports a rather lengthy medical history consisting of unrelenting pain, severe headaches, vertigo, dizziness, flushed face, neck stiffness, cold sweats, upset stomach resulting in frequent nausea and vomiting, extreme sensitivity to light, and generalized paraesthesia that is distributed over his entire neck and trunk.

Diagnosis: RSD (global).

Typical Office Visit: A. S. is greeted and using a wheelchair to make transport easier is helped into a treatment room. On this day, the patient's pain is rated at a 9+ on a numerical pain rating scale 0 to 10 scale (0=no pain, 10=most pain), and is very sensitive to any stimuli, including noise, light, and incidental touching of his body.

The patient remains in the wheelchair and the lights are dimmed to increase his comfort level. A pulse oximeter is placed on his middle finger. His initial heart rate is recorded at 102 beats per minute, fluctuating at ~+/−10 beats (92 to 112 BPM). Red tinted glasses are provided to the patient to even further decrease the level of light stimulation he is receiving. He appears to tolerate wearing the glasses well. The patient rests with the glasses on for 3 minutes. During this time his heart rate decreases fluctuating and stabilizes at about 102 beats per minute.

Warm water is prepared at about 104 degrees F., while the patient remains seated. A collection basin is positioned under his left ear. Using a needleless syringe, 25 ml of warm water is gently squirted into his left ear canal; the water is collected as it flows back out into the basin. This is repeated four times. A. S. tolerates the warm water well. During the caloric stimulation the patient's heart rate lowers to 76 beats per minute with only slight fluctuations. A. S. states that he feels some relief at this point, and is allowed to rest for about three minutes as the next activity is set up.

Next, A. S. is fitted with over-the-ear headphones. The room remains darkened, and the patient continues to wear the red tinted glasses and pulse oximeter as prior. Auditory stimulation is provided to his left ear starting with low frequency tones at a low volume and gradually increasing the volume as well as the frequency until a decrease and stabilization in the heart rate is observed. The patient's heart rate had crept back up to 81 beats per minute as he was being fitted with the headphones. Application of the correct tone brought his heart rate down to and stabilized it at 74 beats per minute. The tone is applied for 30 seconds with a rest of 30 seconds, six times. A. S. tolerates this therapy quite well, and reports his pain to be a 0 on the numerical pain rating scale.

The treatment session's duration, including necessity of taking extra care during the fitting of the therapeutic equipment on the patient due to his lack of tolerance to most stimuli, as well as the patient's needed rest times, is 60 minutes. He left the office asymptomatic and without any assistance needed. A. S. is scheduled to be seen for a follow-up in two days.

Experimental Case Study #1: Hand Replantation

Between 2002 and 2007, hand replantation was performed in three males ranging from 8 to 22 years. While all three males received conventional hand therapy, the third case also received experimental treatment in accordance with some of the techniques described above. At the conclusion of this study, each patient achieved a useful but diminished function of their replanted hand. However, the patient who received the experimental treatment demonstrated better overall functioning, suggesting that cortical configurations in the brain-central nervous system and hand can be externally influenced and even partially restored in the case of hand replantations.

Summary: The aim of this case study was to report on the functional outcomes of non-dominate hand replantation. For the case receiving the experimental treatment, the purpose was to see how the neurocortical, sensory, and motor stimulation described herein affects peripheral nerve regeneration and function outcomes.

The convalescence period was over 12 months for all three cases. Each case noted the return of discriminative sensitivity of the digits. Active finger motion was reported as satisfactory in each case. The case receiving the experimental therapy was the only one to demonstrate intrinsic muscle function. Pinch and grip strength was 40 to 60% less compared to the non-replanted hand. Following the eight week experimental regime, the patient demonstrated dramatic improvement in fine motor control, haptic perception, precision grip control, and sensorimotor-influenced sensation in the fingertips of the replanted hand. The final outcome resulted in this patient having better overall function of the replanted hand.

Evaluation and Treatment: A 21-year-old right-handed Hispanic male had a left hand replanted after being amputated at the forearm in an industrial accident. Although the subject regained movement of all digits following the successful replantation, at pre-treatment for initiation of the experimental therapy, he was experiencing no sensation in the exposed digits of the replanted hand. Although he had re-acquired the ability to grasp, his fine motor coordination and control were significantly impaired. The purpose of this examination was to evaluate the motor sequencing and timing aspects of the upper extremity and hand. Subsequent to a drastic trauma such as amputation, a period of disuse ensues. During such a period changes in the motor centers of the central nervous system occur almost immediately, and begin to lose coherence over time, as well. In the experimental therapy, the optimization of the fine motor functionality can be evaluated and addressed not only from the aspects of dexterity, efficiency of movement and co-ordination, but also as it pertains to sensory-motor processing, and autonomic functional integration. Thus the goal of therapy was to optimize the autonomic regulation of the fuel delivery (i.e. blood flow) to recovering systems and structures, as well as, the supporting structures, and to minimize the degree of dyspraxia and improve hand-eye coordination and the associated central nervous system consequences.

A severed hand completely disrupts the intricate brain-hand connection. Sometimes a "ghost" or "phantom" haptic perception remains. Almost immediately changes in the motor and sensory areas of the brain commence. Over time the coherence within these regions is lost. The faster the hand can be replanted, the better, centrally as well as peripherally.

On the day of the amputation the patient was transferred to a large hospital associated with a university medical program where the replantation was successfully performed. The patient immediately regained gross motor control of his hand with slow, uncertain movements, as well as rudimentary grasping function. He was able to move all digits but lacked dexterity.

As the patient's condition improved he was able to commence standard hand therapy. This consisted of movement, patterning, and repetitive exercises. About six months following the patient's traumatic amputation and replantation, he began the experimental therapy. At pre-treatment, he had re-acquired the ability to grasp, and in fact, grasp stability control with his left hand was nearly average, and he could move all of his fingers using gross motor movements. His fine motor control and precision grip remained significantly impaired; however, the patient was unable to grasp small objects with the distal tips of digits. This precision grip impairment also indicated a significant degree of sensorimotor impairment, a condition that affected the patient's functional haptic perception. The patient also presented with significant dyspraxia especially as it related to sensory-motor processing and sensation. A sensory examination confirmed that no sensation existed in the exposed digits of the replanted hand. The patient was also examined as to joint position sense, two-point discrimination, and vibration calibration. Firing of diffuse sensory receptors was attempted via the application of a TENS unit at its maximum setting, but without immediate results.

The patient initially presented as alert, pleasant, and cooperative for examination. He had a bandage over the wounded wrist and hand with his fingers mobile and exposed. Results obtained from a recent examination by a hand therapist and a handwriting sample was provided, these serving as baseline metrics.

The patient's pulse ox reading was taken per digit. P/O2 measurement of the right hand revealed: thumb 99/73, index finger 98/68, middle finger 97/67, ring finger 98/73, and small finger 99/71. The left hand measurements were 98/73, 98/66, 99/63, 99/69-84 and 99/66-71; a head turn to the left produced 5-7 point variations, proving to be a window of left cerebellar function. Physiological blind spot mapping was performed to identify any decrease in cortical processing as a consequence of decreased sensory information from the affected extremity. Cortical blind spot mapping revealed an enlarged physiological blind spot bilaterally that maximized on the left. This left blind spot measured at 525 square units; top half 258, bottom half 267. A right blind spot was calculated at 653 square units showing 316/337. The increased left blind spot seemed to reflect decreased probability of summation, probably a consequence of decreased afferentation from the injured limb and hand. Additionally the orientation of the visual axis was predictably eschewed; there existed a hyperopia ipsilateral adjacent to the lesion. The find of an enlarged right blind spot was in all probability due to decreased fuel delivery to the left cortex as a consequence of increased alterations in sympathetic tone. This was consistent with the earlier P/O2 findings ipsilaterally with fluctuations of the left hand fuel delivery, again, a likely consequence of decreased ponto-medullary integration secondary to deafferentation from his cerebellum due to the affected upper extremity.

Treatment: A battery of tests was included as part of a second baseline used for initiating and monitoring the experimental therapy. Computerized dynamic posturography (CDP) was performed in order to evaluate integrity of the Parietoinsular vestibular cortex (PIVC) which shares functionality of movements in both hands as well as truncal stability. The patient demonstrated decreased stability and actually fell off the platform in each head position except for left rotation. Aided by application of a TENS unit, the patient was able to complete a 20-second posturography test in all previous head positions.

VENG testing revealed an excycloversional movement of the right eye and incycloversional movement of the left eye on vertical elevation in the dark. An autonomic response on elevation and a depression in reference to pupillary constriction was observed. A computerized metronome sequencing device showed the average number of milliseconds required for the patient to execute a movement. The specific hand and finger activity was physically demonstrated and verbally explained. The patient was asked to push a trigger placed in front of him at eye level. Repetitions were meshed with auditory cues. Execution of motor activity was measured in milliseconds and recorded for all ten fingers, in neutral, left, and right head rotation. A mark made on the floor of the treatment booth served as a positional baseline for fine motor execution. Eye-hand target testing was performed utilizing an eye patch. A notable breakdown in movement when utilizing the uninjured limb with the target presented in the left hemi-field of vision was noted. The patient was markedly less efficient when utilizing the affected limb in both left and right hemi-fields; however the patient was least efficient when using the left upper extremity in the right field of vision. TENS unit application again ensued to summate the parietal area adjacent to the somatotopic hand representation. This allowed the dysdiadokinetic nature of his apraxic limb movements to improve.

Warm caloric irrigation was provided to the patient's left ear to increase middle cerebral arterial blood flow to the contralateral cortex and as a physiological attempt to enhance left hand movement. TENS unit was applied to patient's upper extremity, neck, and face. Visuomotor/visuospatial strategies were utilized. Retraining of eye-hand coordination and motor processing skills were executed via brain sequencing and timing technology.

The patient's pulse rate stabilized at 61-63 beats per minute with his head in neutral and rotated positions. The measurement was taken on the ring finger of the transplanted left hand. Peripheral autonomic function improved, boding well for the healing of tissue and also nerve regeneration. A post treatment handwriting sample was markedly more legible than the earlier one submitted by the patient pre-treatment, indicating cortical improvement.

Following completion of the 8-week experimental regime, a significant degree of sensation and coordination of fine motor control movements including, fine motor control, haptic perception, precision grip control, and sensorimotor-influenced sensation, were largely restored to the subject's replanted left hand.

Experimental Case Study #2: Concussion

An eleven year old female presented for care accompanied by her parents for evaluation of post-concussion syndrome. She sustained a sports related injury about one year earlier while playing basketball. First, she struck her left temporal area against another athlete's shoulder and fell backwards without breaking her fall or bracing herself. She struck the back of her head directly, and then possibly her right shoulder on a hard wood floor. She has made progress with treatment to date, however she remains with residual headaches, and upper neck pain, severe light and sound sensitivity that results in fatigue and increased headache. She describes an unpredictable nature to the onset of symptoms which are aggravated by stress, reading, writing, and traveling in a vehicle. She is sensitive to movement with resultant varying degrees of increased symptomatology after a period of physical activity. Her diagnosis has included concussion syndrome, whiplash, and greater and lesser occipital neuralgia. The patient claims that there is never a period of time where she was asymptomatic since her injury and on a scale of 0 to 10 for numeric pain rating (NPR) describes a typical day as a rated a 2, with her worst days reaching an 8 out of 10. She rates herself a 5 at time of consultation due to the ride to the office.

Interestingly, in the patient's past history she has suffered from TMJ dysfunction which predates the head injury, and has had a history dysautonomia since infancy. The dysautonomia presented in the form of cold lower extremities particularly during cold weather, she will get "purple, cold feet", poor intestinal motility and has suffered from constipation her entire life. She has been on Miralax and other softeners since birth, she has had mild difficulty with food or drink coughing easily since the injury. Alternately she gets very "hot" but does not sweat when she gets stressed or anxious. She denies any fasciculations, involuntary movements, tachycardia, and difficulty starting, stopping or holding her urine. No dry eyes or mouth. She has difficulty sleeping and is taking Neurontin and melatonin however still struggles with her sleep patterns which predictably cause greater headache and fatigue the following day. Additional triggers for the headache and neck pain are identified as cognitive stress, entering a market or mall, seeing lots of people in these crowded environments with immediate increase in symptoms. More delayed reaction is seen with watching television or reading.

Physical examination reveals an alert, cooperative, pleasant appearing 11 year old female who is accompanied by her parents at time of consult and examination. The patient enters the examination room with a forward head carriage and hunched shoulders. She is fatigued quickly during the long exam day and spends much of her time in a slouched posture. Physical examination is unchanged from her prior medical examination and we focus first on functional evaluation. Neurological examination both sensory and motor examination is unremarkable as stated in her prior medical records. During the course of the examination palpations of the sternoclavicular joints were quite painful, greater on the right.

Evaluation of the vestibular or balance system is performed utilizing a CDP Unit. The statistical norms are identified in the literature and the comparison of stability scores are made to similar age and gender individuals. The computerized posturography test identifies the probability of the patient falling due to instability in the central or peripheral nervous systems. The score of 74% or better is the expected normal score for an 11 year old female. The patient's scores were as follows: Neutral head positioning reveals a stability score of 63% with 28% fatigue ratio. Left head rotation 79% with 8% fatigability, right head rotation 73% with 0% fatigue, neck flexion 66% with 0% fatigability, neck extension improved to 72% stability, 0% fatigability.

A pulse oximetry reading was taken. Asymmetry exists which varies with head positioning, VOR activity with a dynamic range in excess of 5-15 beats per minute at rest in neutral seated position. Video nystagmography revealed asymmetry in random saccadic activity, primarily in velocity. No brain sequencing and timing assessment was performed due to her fatigability.

Discussion: A right warm caloric stimulus resulted in a heart rate of 81 BPM with no fluctuation in any labyrinthine positioning and was the most effective stimulation in stabilizing her dynamic range. This suggests its application as an effective modality to increase and stabilize right Ponto-medullary function. Downward OKN and a Right Lower Quadrantinopial Stimulation for 20 seconds improved her posturography scores to 72 and 71% respectively in neutral position as well as lowering her BPM. This supports a diagnosis of right cerebellar/pontine dysfunction with left hemispheric diaschisis. From the history, coincidentally, this is the mother's reported site of impact. Prognosis is guarded.

Treatment: The patient was treated with the goal being to increase her parasympathetic output, stabilize her pontomedullary (PM) system, and additionally decrease the mesencephalic escape. The patient was given a pair of red lenses to decrease the mesencephalic activation through her visual system. The patient was given ear plugs to decrease the auditory input for the same purpose. Application of TENS unit in a right upper extremity montage was performed to increase parietalization of the left cortex. Right VOR stimulation was performed very very slowly with a max of 180 degrees per session. Manipulation of right sternoclavicular joint, left ribs, and upper extremity was performed for afferentation of right cerebellum. This treatment was recommended as a daily home assignment, with visitations at a frequency of 2-3 times per week for 6-8 weeks. The patient's metabolic rate was monitored throughout treatment and she was re-examined weekly.

Two weeks later the patient returned with her mother for initial treatment. The goal as explained was to begin to regulate the PM system as identified by narrowing the 20-30 BPM swings in heart rate with alteration in head position while at rest or even, as has been evident, while at rest with head in neutral position. The treatment applied was to the right cerebellum and Ponto-medullary system. The patient was treated with: 1) Right VOR spin which is more tolerable and effective with fixation. 2) Manipulation of the right ribs. 3) Warm right caloric stimulus. 4) Red filtered lens. 5) Ear plugs. 6) Gyroscope for increased cerebellar feedback. 7) Placing the right lower extremity in a bucket of warm water to increase small diameter afferent nerve feedback to PIVC. She tolerated treatment well, and remained between a 3.5 to 4.5 NPR. She was seen for 75 minutes in the morning and 60 minutes with intermittent breaks in the afternoon.

The experimental treatment progressed with regular visitations. At each session, the patent received the same seven stimuli described above, tolerated the treatment well, and reported a consistent NPR of between 3.5 and 4.5. The patient showed slow signs of improvement, mentioning that her sleep had improved and appearing to be more upbeat, less fatigued, and more tolerant to ambient light in the clinic.

On the ninth visit, the patient returned for follow-up and was treated recumbently. She maintained her heart rate at 83-85 BPM throughout the session with electric stimulation, temperature stimulation, labyrinthine activity, and active and passive ranges of motion of the cervical spine with only 1-2 point increases in BPM. She did not complain in recumbent posture with passive positioning of the head— only 2 mild reports of pain during active unassisted head repositioning. She again had less of a reaction to pain during VOR which succeeded for 360 degrees. The patient continued to have daily bowel movements without Miralax. She maintained the same P/O2 for the lower extremities as upper and there was no turning purple of the lower extremities as the autonomic challenge of ice application was successful. The experimental treatment was applied with the patient in the recumbent position, and the patient tolerated it well, remaining between a 3.5 to 4.5 NPR.

The next day, the patient returned and noted that she had taken it easy over the weekend and felt the same reported NPR 3 to the neck and 4 to the headache, however the ride was more tolerable as she was half way through her commute before she felt the ill effects of the car ride as well as light sensitivity as it was a very bright day. When asked if she noticed any decrease in light or sound sensitivity she replied "not really" or "I do not know" but then realized she tolerated the car ride involving the two components that are disturbing to her. She had many questions regarding the improved autonomic outcomes which are demonstrated by her no longer requiring Miralax to have a bowel movement, whereas since infancy she would be 3-4 days constipated and require the laxative. Additionally the minimal if not absent discoloration of the lower extremities, even when challenged with ice packs, is quite impressive as compared to the initial visit. The scheduled treatment was performed with the patient supine, and the heart rate was at 81 BPM supine with no fluctuation on labyrinthine activity or VOR spin.

The patient returned the next day with mom for follow-up treatment. The patient was ebullient and quite happy. She claimed her head pain was a 3.5 and her neck pain was a 3. She had a resting heart rate of 85 BPM seated, 81 BPM supine. The heart rate did not fluctuate with head movement supine and only 1-2 beats seated. Treatment in the morning session consisted of SOT technique, TENS application, activator to C1, occiput and C2 on the right. Post treatment recheck in seated posture showed her heart rate was 76-80 BPM with increased VOR activity to 2 turns without change in BPM and no reporting of headache. Resistance to muscle testing produced no change in BPM supine in either extremity. Once the observation of improvement was made the patient changed her disposition, although less so than prior week's reaction and noted headache after the progress is pointed out. Also, turning on the fluorescent light did not cause a spike in BPM and was tolerable although accompanied by squinting.

The patient returned the next day. Treatment was the same, except the warm right caloric stimulus was replaced by left cortical efferent activities (i.e., performing a subtraction) and the warm water immersion was replaced by TENS application to increate parietalization. The patient tolerated treatment well in this session and the following one.

Six days later, the patient returned and noted improvement from last visit as she was more cheerful, and did not complain as much in terms of discomfort to palpation, movement of the cervical spine, or increased stimulation. She tolerated progressively faster VOR activity and completed three revolutions without discomfort but noted pressure building on the initiation of the fourth. She mounted and dismounted the treatment table in a prone and supine position which required she extend the cervical spine which she did pain-free. When queried she indicated clearly that there is pain "only sometimes", in extension at the end range of motion. She claimed and acknowledged that rotation and flexion are not painful. The patient added interactive metronome training to the regimen.

Two visits later, the patient returned from riding the escalator at the airport in an attempt to stabilize otolithic activity, and we identified that downward translation is causing the mesencephalic escape. She was able to climb and descend the escalator well twice without complaint, fatigue, or apparent discomfort with application of TENS on the right. The treatment added pictures to subtraction as a left cortical efferent activity, and eliminated the use of TENS.

Three days later, the patient reported a breakthrough weekend where she was able to visit a mall 12 miles away and ride the escalator several times and walk a great distance successfully. The escalator ride was successful while applying the TENS unit on the right hand side—this mitigated the pain and headache. The patient's father and mother reported she had a greater amount of energy and better disposition over the weekend.

On the twentieth visit, the patient reported completing a successful evening dining out that included significant multimodal stimulation that she previously was unable to complete, even with severe humidity and weather conditions affecting the vestibular system. The patient managed the evening dinner which included conversation and ambient noise demonstrating increased toleration in her auditory and visual processing abilities and metabolic capacity. The patient reported good energy and interaction throughout. The morning session was increased to 90 minutes of treatment, while the afternoon session remained at 60 minutes with intermittent breaks. This pattern remained throughout the remainder of the therapy.

Over the next several visits, the patient was able to ride escalators without TENS application, add to the number of therapeutic repetitions she was able to perform with improving fatigability, make significant gains in endurance and level of activity (both physical and cognitive), and cautiously incorporate pre-injury functions. Subsequently, the patient was able to drive to the clinic without TENS application, and perform home activities with less fatigue. The mother felt that there were flashes of the old (patient) returning in both activity and disposition.

On the twenty-sixth visit, the patient reported headache bitemporally and occasionally frontal with transient neck discomfort and milder light sensitivity than previously. These residual symptoms did not increase, however, and there had been a significant increase in her physical and cognitive activities, in addition to other gains.

At this time, in comparison to the initial evaluation:

1) Dysautonomia is considerably improved as she no longer has discoloration of the lower extremities even with temperature challenge. There is minimal discoloration around the nail beds of the large toe occasionally on inspection after temperature challenge.

2) The patient no longer experiences "hot" episodes with no sweating.

3) For the past several weeks, the dynamic range of her pulse oximetry has remained around 80 BPM with acceptable fluctuation of 1-3 BPM with labyrinthine activity, cervical motion or VOR activity suggesting stabilization of the VOR mechanism and the related brain stem functions.

4) There is improved GI function as she is no longer dependent on Miralax and is having daily bowel movements.

5) Additionally, the mother notes that the fatigability from rehab sessions and homework activities is markedly less draining and the time to recovery is noticeably shorter.

6) Her reading capacity has increased to 45 minutes to date. The patient is also watching television for periods of 30 minutes 3 times per day (with normal volume setting) with no adverse reaction.

7) She is able to successfully negotiate elevators, escalators and moving walkways with greater stability and endurance. We identified the deficit in the downward translational vector which produced a significant headache on initial attempt and she is now able to successfully perform 20 consecutive repetitions. This differentiates the utricular/saccular from canal components of the right cerebellar deficit.

8) The patient is capable of withstanding the 1 hour drive with partial use of a TENS which we are phasing out this week.

9) The patient is demonstrating decreased auditory sensitivity as the volume setting on the sequencing and timing equipment has progressively been raised to near 50% max volume. This was done progressively without patient complaint. This translated into the patient being able to tolerate social activity over the past 2 weeks progressing to dinner out with family and trips to the mall in the continued rehab protocol.

10) The patient no longer has sterno-clavicular pain and there is complete ROM of the cervical spine. Her identified area of tenderness no longer involves the occipital area primarily but the mid cervical spine as she has less of a forward head carriage and is developing more appropriate cervical biomechanics. Palpation is more tolerable.

11) The patient has improved disposition as the mother notes her old personality is returning.

12) Finally, the patient is now sleeping through the night and the mother is inquiring if and when her medication may be titrated down.

On the twenty-seventh visit, the patient willingly removed her red filtered glasses during portions of the interactive metronome training. By the thirty-second visit, the patient willingly removed her red-tinted glasses for all tasks. The therapy assistant has been noting that the patient has a sunny disposition. By the thirty-fifth visit, the patient no longer asks that the lights be turned off during various tasks/ manipulations. By the thirty-seventh visit, the patient appears happier and does not complain of headaches or alternate pain.

On the thirty-ninth visit, the patient, her mother spent an hour in the parking lot waiting. Throughout that time, the patient was not sensitive to either the bright sunlight or relative heat. The treatment concluded after 43 visits, with the patient cheerful and talkative during the last several sessions.

Proposed Explanation

A proposed explanation for the success of the methods described in this application is as follows.

Examination of any patient should begin with an evaluation of the autonomic nervous system. The autonomic nervous system (ANS) is the foundational tenant and prerequisite for basic life functioning. Contained within the central and peripheral nervous systems, the ANS delivers fuel to both the brain and the body and modulates the functional interaction between these two systems. The ANS also acts as a mediator between the environment and the internal organism, reacting to external stimulation with vital processes that are typically homeostatic. These involuntary physiological responses and associated internal changes are a part of the body's behavior that is structured, where possible, to achieve a healthy physiology. For example, when an area of the nervous system or brain is stimulated, a physiological response is elicited. If the autonomic response is congruent with expected neurophysiology, the system is deemed intact. Conversely, if the stimulation elicits an aberrant physiological response, the aberrant response may be indicative of a pathological dysregulation. Examining autonomic regulation in this manner allows a clinician to identify the probability and/or existence of dysfunction, injury, or disease within the nervous system or body. However, until the methods presented in this application, an evaluative approach as described herein has not been the starting point of rehabilitative services.

Since the greatest probability for a patient's recuperative success depends directly upon the functioning of her autonomic nervous system, Cortical Integrative Therapy (CIT), in accordance with the methods of the present invention, begins as a diagnostic process with an examination of the ANS. By utilizing the physiological windows of observation, CIT clinicians determine the stability or instability of a patient's autonomic nervous system. Windows of physiological measurement for use in determining response to ANS stimulation in accordance herewith include heart rate, blood pressure, pseudo motor activity, oxygenation, sweating, and peripheral angiography. Pulse-oximetry is a standardized procedure for monitoring heart rate and oxygen saturation of normal and dynamic neurophysiology. Statistical norms in resting physiology and physiological change/challenge are also understood as indicators of autonomic stability. The CIT clinician links the symptom(s) back to the loss of normal neuro-physiology with consideration to the specific inhibitory mechanism(s) and/or excitatory mechanism(s) or the balance of inhibitory and excitatory mechanisms which permit the dysfunction.

One possible conceptual framework for rehabilitation in accordance with the methods described herein may be found in the emergent concept of Dr. Antonio Damasio's brain-body maps. See, for example: Damasio, Antonio R. *Looking for Spinoza: Joy, Sorrow, and the Feeling Brain* (Harcourt, 2003); Damasio, Antonio R. *Descartes' Error: Emotion, Reason, and the Human Brain* (Penguin, 2005); and Damasio, Antonio R. et al., "Minding the Body". *Daedalus* 135.3 (2006): 15-22. Another possible framework is provided by Dr. Rodolfo Llinás and his brain timing mechanisms. See, for example: Llinás, Rodolfo et al., *The Mind-Brain Continuum: Sensory Processes* (Bradford Books, 1996); Llinás, Rodolfo (1998). "The neuronal basis for consciousness". Phil. Tran. R. Soc. Lond. (The Royal Society) 353: 1841-1849; Llinas, Rodolfo (1999). "Thalamocortical dysrhythmia: a neurological and neuropsychaitric syndrome characterized by magnetoencephalography". PNAS 96 (26): 15222-15227; Llinás, Rodolfo R. *I of the Vortex: From Neurons to Self* (MIT Press, 2001); Llinás, Rodolfo (2002). "Temporal binding via coincidence detection of specific and nonspecific thalamocortical inputs: A voltage-dependent dye-imaging study in mouse brain slices". PNAS (The National Academy of Sciences) 99 (1): 449-454; see also Jones, Edward G. "Thalamocortical dysrhythmia and chronic pain". *Pain* (Elsevier) 150: 4-5. 2010 and citations therein. Understanding of the phenomenon of coherence may also inform understanding of the underlying mechanisms. The articles cited in this paragraph are incorporated by reference as if set forth in their entirety herein.

Consistent with the methods described in this application, important stages of Cortical Integrative Therapy (CIT) include the following:

Stage 1: Stabilize autonomics;

Stage 2: Build metabolic capacity within the ANS;

Stage 3: Build adaptive plasticity in the injured or compromised system; and

Stage 4: Reintegration strategy into other rehabilitative modalities.

Stage 4 is the implementation of specific strategies to restore ANS performance as closely as practicable to norms associated with healthy physiology as understood by present day neuroscience. As cited above, Dr. Rodolfo Llinás, MD, PhD, has shown that many of the higher brain functions, including consciousness, are products of the timing of the constant oscillations that exist between the thalamus and the rest of the brain. This is a loop of signals from the thalamus to cortical regions and a return of signals from the various sensory processing areas of the brain. Higher functions, including consciousness, exist when these oscillations are synchronized. This allows the processing centers of the brain to assemble the disparate intrinsic and extrinsic data into a cohesive whole, a process known as temporal binding.

The frequencies of the oscillations are dependent on the state of brain activity including mental activity. This central state is regulated by the thalamus' gating activity on the sensory information that reaches the cortex as well as the thalamus' own feedback control of the loops to said cortices. Thalamic neurons that are typically involved with this process are: thalamo-cortical, thalamo-reticular, and thalamic interneurons.

The oscillatory feedback process begins in oscillatory cells within the thalamus, which have input from somatosensory pathways and feedback pathways that are intrinsic to the brain. These thalamic oscillatory cells are highly responsive, and change accordingly to the dynamic nature of the inputs they receive. The greatest modulation of these feedback loops is from inhibitory interneurons that are within the thalamic reticular nucleus and the cortex. Also, when a particular region of the cortex is involved in a thalamocortical feedback loop, which appears to be columnar in nature, the adjacent columnar areas are actively inhibited. This has the effect of physically separating oscillation resonance pathways from each other. Multiple thalamocortical loops are able to occur simultaneously throughout many different regions of the brain during conscious activity. The synchronization of these oscillations between the different regions of the brain allow for cohesive functioning that is associated with specific brain activities, mental states, and consciousness. When these oscillatory feedback processes are not properly synchronized a strong association has been shown with cognitive disorders, neuropathic pain, tinnitus, Tourette's, as well as Parkinson's disease. CIT creates a starting point and monitoring strategy to ensure the optimal rehabilitative outcomes.

The embodiments of the invention described above are intended to be merely exemplary; numerous variations and modifications will be apparent to those skilled in the art. All such variations and modifications are intended to be within the scope of the present invention as defined in any appended claims.

What is claimed is:

1. A method of treating a subject with traumatic brain injury by stimulation of afferent fibers so as indirectly to cause improvement in the area of the brain affected by the injury, and in overall brain function, the method providing a protocol comprising:
    selecting a plurality of distinct postures, to be sequentially assumed by the subject, from a posture set of walking, standing, sitting, and supine;
    selecting a plurality of distinct stimuli, to which the subject will be sequentially subjected, from a stimulus set of TENS, non-painful heat, non-painful cold, visual, occulomotor stimulation, crude touch, olfactory stimulation, vestibular stimulation, and auditory stimulation;
    having the subject sequentially assume each selected posture;
    in each of the selected postures,
        subjecting the subject to each of the selected stimuli sequentially, while measuring a set of autonomic physiological responses of the subject, to such stimulation, the set having at least one member and selected from the group consisting of oxygen saturation, heart rate, pupillary response, blood pressure, sweat production, pseudomotor activity, and respiration;
    evaluating the autonomic physiological responses in each of the selected postures to identify the posture wherein the autonomic physiological responses of the subject exhibit a least amount of dysfunction relative to corresponding statistical norms for such responses;
    identifying the stimulus with respect to which the autonomic physiological responses of the subject exhibit a change in the amount of dysfunction towards corresponding statistical norms for such responses when in the identified posture;
    repeatedly subjecting the subject to the identified stimulus while the subject is in the identified posture until a desired endpoint physiological condition is achieved in which the autonomic physiological responses to the identified stimulus approach a state of normalcy relative to corresponding statistical norms for such responses;
    upon achieving the desired endpoint physiological condition, for at least one posture different from the identified posture, subjecting the subject to a stimulus selected from the stimulus set and determining whether the autonomic physiological responses of the subject to the stimulus selected at the different posture exhibit dysfunction relative to corresponding statistical norms for such responses; and
    upon existence of such a dysfunction, repeatedly subjecting the subject to the stimulus selected at the different posture until a further desired endpoint physiological condition is achieved in which the autonomic physiological responses to the stimulus selected at the different posture approach a state of normalcy relative to corresponding statistical norms for such responses,
    wherein the foregoing protocol promotes thalamocortical pathways within the brain.

2. The method according to claim 1, wherein subjecting the subject sequentially to each of the selected stimuli includes, for each selected stimulus, varying at least one parameter of the stimulus, the parameter selected from the group consisting of amplitude, frequency, and duration of the stimulus, and
    wherein identifying the stimulus with respect to which the autonomic physiological responses of the subject exhibit a least amount of dysfunction when in the identified posture further includes identifying a parameter value, associated with the at least one parameter of the stimulus, with respect to which the subject exhibits a least amount of dysfunction relative to corresponding statistical norms for such responses.

3. The method according to claim 1, wherein the desired endpoint physiological condition is a condition wherein subjecting the subject to a stimulus from the stimulus group, other than the identified stimulus, does not cause dysfunction in the subject while the subject is in the identified posture.

4. The method according to claim 1, wherein if no dysfunction in the subject exists while the subject is in the at least one posture different from the identified posture, the method further comprises:
    performing additional therapeutic modalities to facilitate further enhancement of physiological condition.

5. The method according to claim 1, wherein the traumatic brain injury includes post-concussion syndrome (PCS).

6. The method according to claim 5, wherein the post-concussion syndrome is associated with at least one symptom selected from the group consisting of headaches, dizziness, neck pain, stiff neck, nervousness, fatigue, irritability, cold sweats, excessive eye sensitivity to light and combination thereof, and wherein the treatment results in a decrease in the at least one symptom.

7. The method according to claim 1, wherein quantitatively measuring an autonomic physiological response parameter as of when the subject has been subjected to each of the selected stimuli includes performing at least one measurement selected from the group consisting of Video Electronystagmography, pulse oximetry, Computerized Dynamic Posturography and combinations thereof.

* * * * *